US006562569B1

(12) United States Patent
Dale

(10) Patent No.: US 6,562,569 B1
(45) Date of Patent: *May 13, 2003

(54) ARRAYS WITH MODIFIED OLIGONUCLEOTIDE AND POLYNUCLEOTIDE COMPOSITIONS

(75) Inventor: Roderic M. K. Dale, Wilsonville, OR (US)

(73) Assignee: Oligos Etc. Inc., Wilsonville, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/524,092

(22) Filed: Mar. 13, 2000

Related U.S. Application Data

(63) Continuation-in-part of application No. 09/408,088, filed on Sep. 29, 1999, now Pat. No. 6,087,112, which is a continuation-in-part of application No. 09/223,498, filed on Dec. 30, 1998, now abandoned.

(51) Int. Cl.$^7$ ............................ C12Q 1/68; C07H 21/04

(52) U.S. Cl. ......................... 435/6; 536/23.1; 536/24.3; 435/77; 435/78

(58) Field of Search ............................ 435/6; 536/23.1, 536/24.3; 935/77, 78

(56) References Cited

U.S. PATENT DOCUMENTS

| | | |
|---|---|---|
| 5,436,327 A | 7/1995 | Southern et al. |
| 5,445,934 A | 8/1995 | Fodor et al. |
| 5,492,806 A | 2/1996 | Drmanac et al. |
| 5,525,464 A | 6/1996 | Drmanac et al. |
| 5,556,752 A | 9/1996 | Lockhart et al. |
| 5,631,734 A | 5/1997 | Stern et al. |
| 5,695,940 A | 12/1997 | Drmanac et al. |
| 5,700,637 A | 12/1997 | Southern |
| 5,723,320 A | 3/1998 | Dehlinger |
| 5,750,669 A | 5/1998 | Rosch et al. |
| 5,770,722 A | 6/1998 | Lockhart et al. |
| 5,831,070 A | 11/1998 | Pease et al. |
| 5,837,832 A | 11/1998 | Chee et al. |
| 5,843,655 A | 12/1998 | McGall |
| 5,856,174 A | 1/1999 | Lipshutz et al. |
| 5,861,242 A | 1/1999 | Chee et al. |
| 5,872,232 A | 2/1999 | Cook et al. ............... 536/23.1 |
| 5,919,523 A | 7/1999 | Sundberg et al. |
| 6,087,112 A * | 7/2000 | Dale ............................ 435/6 |

FOREIGN PATENT DOCUMENTS

| | | |
|---|---|---|
| EP | 0 373 203 B1 | 8/1994 |
| EP | 0 742 287 A2 | 11/1996 |
| WO | WO 90/10716 | 9/1990 |
| WO | WO 93/17126 | 9/1993 |
| WO | WO 94/15619 | 7/1994 |
| WO | WO 95/11995 | 5/1995 |
| WO | WO 95/35505 | 12/1995 |
| WO | 98/00564 | 1/1998 |
| WO | 98/02582 | 1/1998 |
| WO | 98/13526 | 4/1998 |
| WO | 98/39348 | 9/1998 |
| WO | 00/40525 | 7/2000 |

OTHER PUBLICATIONS

Lendell L. Cummins et al., "Characterization of fully 2'–modified oligoribonucleotide hetero– and homoduplex hybridization and nuclease sensitivity.", Nucleic Acids Research, (1995) vol. 23, No. 11, pp. 2019–2024, XP 002048574.

Harold M. Moody et al., "Regiospecific inhibition of DNA duplication by antisense phosphate–methylated oligodeoxynucleotides." Nucleic Acids Research, (1989), vol. 17, No. 12, pp. 4769–4782, XP 002166143.

Chalifour, Lorraine E., et al., "A Method for Analysis of Gene Expression Patterns," *Analytical Biochemistry* (1994) vol. 216:299–304.

DeRisi, Josepeh L., et al., "Exploring the Metabolic and Genetic Control of Gene Expression on a Genomic Scale," *Science* (Oct. 24, 1997) vol. 278:680–686.

Ehlers, Stefan, et al., "Differentiation of T Cell Lymphokine Gene Expression: The In Vitro Acquistion of T Cell Memory," *J. Exp. Med.* (Jan. 1991) vol. 173:25–36.

Glaser, Vicki, "Rosetta Inpharmatics chips in," *Nature Biotechnology* (Oct. 1997) vol. 15:937–938.

Goodwin, Raymond G., et al., "Human Interleukin 7: Molecular Cloning and Growth Factor Activity on Human and Murine B–Lineage Cells," *Proc. Natl. Acad. Sci. USA* (Jan. 1989) vol. 86:302–306.

Goodwin, Raymond G., et al., "Cloning of the Human and Murine Interleukin–7 Receptors: Demonstration of a Soluble, Form and Homology to a New Receptor Superfamily," *Cell* (Mar. 23, 1990) vol. 60:941–951.

Hoheisel, Jörg D., "Oligomer–chip Technology," *TibTech* (Nov. 1997) vol. 15:465–469.

Leonard, Warren J., et al., "Molecular Cloning and Expression of cDNAs for the Human Interleukin–2 Receptor," *Nature* (Oct. 1984) vol.311:626–631.

Lockhart, David J., et al., "Expression Monitoring by Hybridization to High–Density Oligonucleotide Arrays," *Nature Biotechnology* (Dec. 1996) vol. 14: 1675–1680.

(List continued on next page.)

Primary Examiner—Andrew Wang
Assistant Examiner—James Douglas Schultz
(74) Attorney, Agent, or Firm—Morgan, Lewis & Bockius LLP

(57) ABSTRACT

The present invention provides arrays having associated modified oligonucleotides that selectively bind to DNA or RNA, methods of making such arrays, assays for using such arrays, and the like. In one embodiment, the arrays of the invention exhibit an increased binding affinity with complementary nucleic acids, and in particular with complementary RNA. In another embodiment, the associated nucleic acids of the array of the invention exhibit substantial acid resistance, allowing the arrays to be treated with low pH solutions. In another embodiment, the modified associated nucleic acids of the array of the invention exhibit substantial resistance to nuclease degradation.

18 Claims, 1 Drawing Sheet

OTHER PUBLICATIONS

Marshall, Andrew, et al., "DNA Chips: An Array of Possibilities," *Nature Biotechnology* (Jan. 1998) vol. 16:27–31.

Nguyen, Catherine, et al., "Differential Gene Expression in the Murine Thymus Assayed by Quantitative Hybridization of Arrayed cDNA Clones," *Genomics* (1995) vol. 29:207–216.

Nishi, Tatsunari et al., "Cloning and Expression of a Novel Variant of Human Interferon–γ cDNA," *J. Biochem* (1985) vol. 97:153–159.

Ramsay, Graham, "DNA Chips: State of the Art," *Nature Biotechnology* (Jan. 1998) vol. 16:40–44.

Schena, Mark, et al., "Parallel Human Genome Analysis: Microarray–Based Expression Monitoring of 1000 Genes," *Proc. Natl. Acad. Sci. USA* (Oct. 1996) vol. 93:10614–10619.

Shalon, Dari, et al., "A DNA Microarray System for Analyzing Complex DNA Samples Using Two–Color Flourescent Probe Hybridization," *Genome Research* (1996) vol. 6:639–645.

Zhao, Nanding, et al., "High–Density cDNA Filter Analysis: A Novel Approach for Large–Scale, Quantitative Analysis of Gene Expression," *Gene* (1995) vol. 156:207–213.

* cited by examiner

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
-continued

<400> SEQUENCE: 1
ggtggttcct cctcagtcgg                                                    20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ccgactgaga aggaaccacc                                                    20
```

ARRAYS WITH MODIFIED OLIGONUCLEOTIDE AND POLYNUCLEOTIDE COMPOSITIONS

This application is a continuation-in-part of our earlier filed application Ser. No. 09/408,088, filed Sep. 29, 1999, now U.S. Pat. No. 6,087,112, which is a continuation-in-part of application Ser. No. 09/223,498, filed Dec. 30, 1998, now abandoned, to each of which we claim priority under 35 U.S.C. §120 and which are each incorporated herein by reference in their entirety.

FIELD OF THE INVENTION

The field of this invention is arrays having associated modified oligonucleotides and/or polynucleotides, methods of producing such arrays, and uses thereof.

BACKGROUND OF THE INVENTION

Arrays of binding agents, such as oligonucleotides and polynucleotides, have become an increasingly important tool in the biotechnology industry and related fields. These arrays, in which a plurality of binding agents are deposited onto a solid support surface in the form of an array or pattern, find use in a variety of applications, including drug screening, nucleic acid sequencing, mutation analysis, and the like. One important use of arrays is in the analysis of differential gene expression, where the expression of genes in different cells, normally a cell of interest and a control, is compared and any discrepancies in expression are identified. In such assays, the presence of discrepancies indicates a difference in the classes of genes expressed in the cells being compared.

In methods of differential gene expression, arrays find use by serving as a substrate with associated binding fragments such as oligonucleotides. Nucleic acid sequences are obtained from analogous cells, tissues or organs of a healthy and diseased organism, and hybridized to the immobilized set of binding fragments associated with the array. Differences between the resultant hybridization patterns are then detected-and related to differences in gene expression in the two sources.

A variety of different array technologies have been developed in order to meet the growing need of the biotechnology industry. Despite the wide variety of array technologies currently in preparation or available on the market, there is currently no technique for distinguishing the type of binding partner that recognizes a probe sequence on an array (i.e. the ability to distinguish the difference between a target RNA and target DNA sequence). Such an ability would, for example, allow the detection of RNA transcription directly from a cell or tissue without separating the RNA from the DNA. In addition, it would allow the detection of an amplification of specific DNA sequences, e.g., the amplification of an oncogene in a cancer.

There is thus a need in the art for an array that can distinguish between the presence of an RNA molecule and a DNA molecule having identical sequences.

SUMMARY OF THE INVENTION

The present invention provides arrays having associated oligonucleotide and/or polynucleotides with modified structures that confer preferential binding to either RNA or DNA relative to the other methods of making such arrays, and assays for using such arrays. The arrays of the present invention have compositions composed of individual polymers that bind selectively to DNA, compositions of individual polymers that bind selectively to RNA, or preferably compositions of each within a single array. The invention comprises an array device comprised of a support surface and polymer molecules bound to the support surface. The polymer molecules are not naturally occurring oligonucleotides or polynucleotides, but rather have modified internucleoside and/or ribose structures with bases attached in the desired sequential positioning and the desired spacing between the bases. The specific modifications allow not just the identification of a particular sequence, but also the identification of the particular type of nucleic acid (i.e. DNA or RNA) having the complementary sequence. Although an array of the invention will have modified oligonucleotides therein arrays of the invention do not exclude the presence of natural oligonucleotides which might also be present to provide comparative information.

In one embodiment, the modified, stably associated polymers of the arrays of the invention preferably recognize RNA. For example, compositions of the arrays have multiple polymers having at least one 2'-5' internucleoside linkage. In a preferred embodiment, the modified polymers of the compositions of the array are comprised of monomer units with 2'-5' internucleoside linkages have a plurality of monomer units in the polymer with a 3'-substitution (e.g., a 3'-O-methyl substitution).

In another embodiment, the modified, stably associated polymers of the invention selectively recognize DNA. For example, polymers having at least one p-ethoxy backbone linkage internucleoside linkage bind preferentially to DNA relative to a corresponding RNA sequence.

In a particularly preferred embodiment, the array of the invention is composed of both modified polymer compositions that selectively bind to RNA relative to DNA and modified polymers that selectively bind to DNA relative to RNA. In a particularly preferred embodiment, a single array can have a composition that selectively binds to RNA relative to a corresponding DNA sequence and a composition that selectively binds to DNA relative to a corresponding RNA sequence where the polymers of both of these compositions have the same (meaning corresponding) base sequence for hybridization. This allows a direct comparison of the binding of the two compositions, and will allow a direct determination of the nature of the nucleic acids present in a sample. The array may further comprise corresponding DNA and/or RNA sequences which are not modified.

The compositions of the arrays of the invention are also preferably end-blocked to provide nuclease resistance to the compositions of the array. This allows the arrays to be directly exposed to biological samples which contain nucleases without disrupting the integrity of the array compositions. In addition, nucleases can be used to digest the test substrate binding agent, freeing the associated binding agents for further use. The chemical modification may be on the 5' end for modified oligonucleotides and/or polynucleotides attached to a substrate at the 3' end, or alternatively the chemical modification may be on the 3' end for modified oligonucleotides and/or polynucleotides attached to a substrate at the 5' end. The associated modified oligonucleotides and/or polynucleotides remain unaffected as to the binding capacity of the associated oligonucleotides. The end block can be placed on modified and/or unmodified sequences on the array.

These arrays also offer the significant advantage that the individual chip can be tested for efficacy and/or quality prior to use with a test sample, which is particularly helpful if the amount of test sample is limited or if the array is being used as a medical device and must comply with FDA quality control requirements.

The invention provides an array that is composed of multiple beads each having associated modified oligonucleotides and/or polynucleotides. Preferably, these beads have a density greater than water and can be centrifuged out of solution or are magnetic to allow the identification and isolation of particular nucleic acid species.

The present invention further provides an assay using the arrays of the invention to determine physiological responses such as gene expression, where the response is determined by the hybridization pattern of the array after exposure to test samples. The test samples may be mRNA, cDNA, whole cell extracts, and the like.

It is an advantage of the associated modified oligonucleotides and/or polynucleotides of the arrays of the invention that the chemical modifications enhance specific chemical binding interactions, e.g., display a differential affinity for RNA or DNA. This allows an array not only to identify the presence of a nucleic acid having a specific sequence in a sample, but also to recognize whether the complementary nucleic acid is RNA or DNA.

It is an advantage of the associated modified oligonucleotides and/or polynucleotides of the invention that the acid stable modifications confer an improved stability on the modified oligonucleotides and/or polynucleotides in an acidic environment (e.g., as low as pH of 1 to 2).

It is another advantage of the associated modified oligonucleotides and/or polynucleotides of the invention that they bind with specificity to specific test nucleic acids.

It is an object of the invention that the modified oligonucleotides and/or polynucleotides can be used in a variety of array applications, such as identification of new genes, determination of expression levels, diagnosis of disease, and the like.

These and other objects, advantages, and features of the invention will become apparent to those skilled in the art upon reading the details of the modified oligonucleotides and/or polynucleotides and uses thereof as more fully described below.

DETAILED DESCRIPTION OF THE PREFERRED EMBODIMENTS

Figure 1:
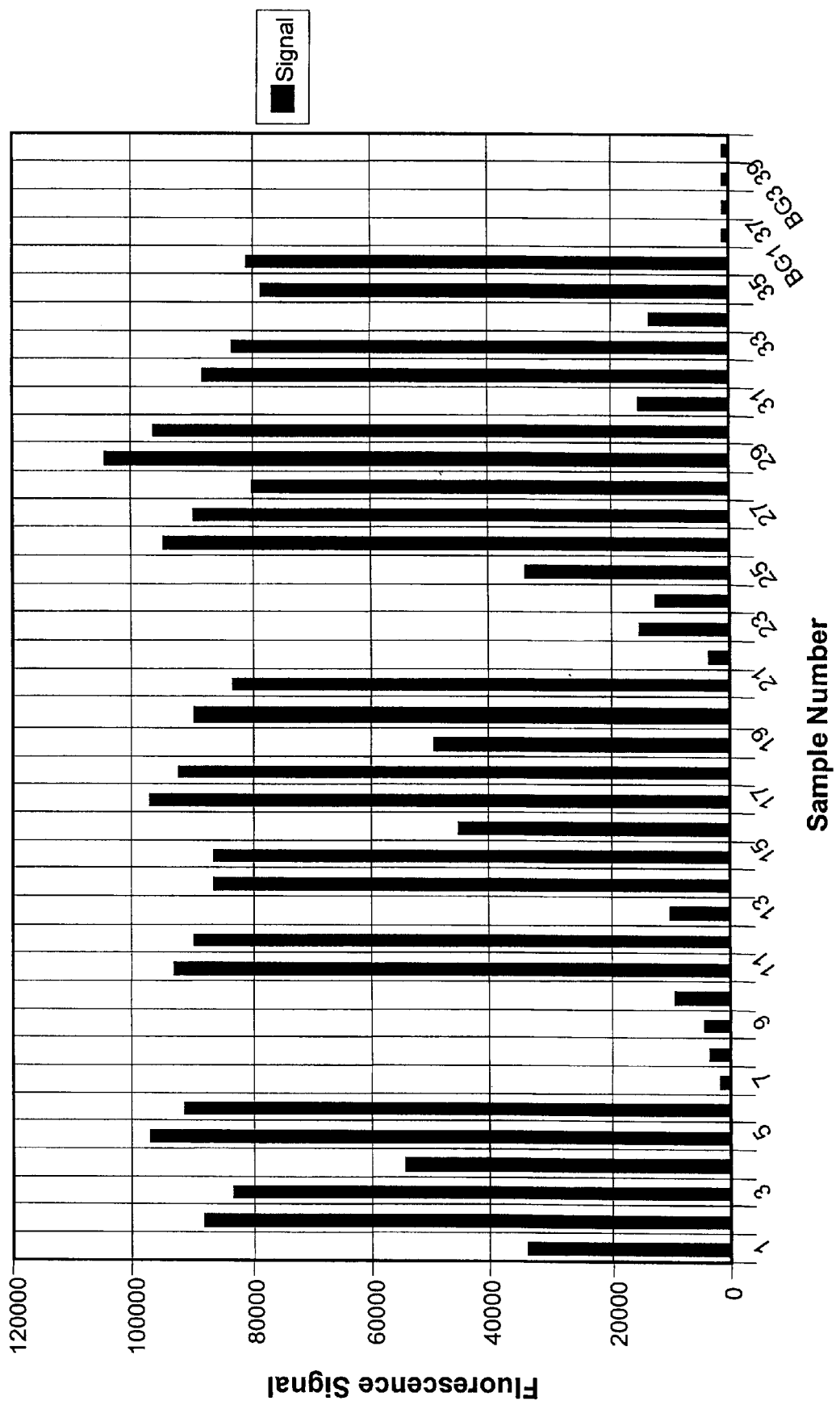
FIG. 1 is a bar graph illustrating the ability of polymers having different backbones to bind to RNA and DNA. The sample numbers of the FIGURE are as in Example 3.

It is to be understood that this invention is not limited to the particular methodology, support surfaces, materials and modifications described and as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "and", and "the" include plural referents unless the context clearly dictates otherwise. Thus, for example, reference to "an oligonucleotide" may include a plurality of oligonucleotide molecules and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned are incorporated herein by reference for the purpose of describing and disclosing, for example, materials, constructs, and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Definitions

The terms "nucleic acid" and "nucleic acid molecule" as used interchangeably herein, refer to a molecule comprised of one or more nucleotides, i.e., ribonucleotides, deoxyribonucleotides, or both. The term includes monomers and polymers of ribonucleotides and deoxyribonucleotides, with the ribonucleotides and/or deoxyribonucleotides being connected together, in the case of the polymers, via 5' to 3' linkages.

Polymers of the invention are modified nucleic acids and internucleoside linkages may include any of the linkages known in the nucleic acid synthesis art including, for example, nucleic acids comprising 5' to 3' linkages and/or 5' to 2' linkages. The nucleotides used in the nucleic acid molecule may be naturally occurring or may be synthetically produced analogues that are capable of forming base-pair relationships with naturally occurring base pairs. Examples of non-naturally occurring bases that are capable of forming base-pairing relationships include, but are not limited to, aza and deaza pyrimidine analogues, aza and deaza purine analogues, and other heterocyclic base analogues, wherein one or more of the carbon and nitrogen atoms of the purine and pyrimidine rings have been substituted by heteroatoms, e.g., oxygen, sulfur, selenium, phosphorus, and the like.

The term "oligonucleotide" as used herein refers to a nucleic acid molecule comprising from about 2 to about 300 nucleotides. Oligonucleotides for use in the present invention are preferably from 6–200, more preferably from 15–150 in length.

The term "polynucleotide" as used herein refers to nucleic acid molecules comprising a plurality of nucleotide monomers including but not limited to nucleic acid molecules comprising over 200 nucleotides.

The terms "modified oligonucleotide" and "modified polynucleotide" as used herein refer to oligonucleotides and/or polynucleotides with one or more chemical modifications at the molecular level of the natural molecular structures of all or any of the bases, sugar moieties, internucleoside phosphate linkages, as well as to molecules having added substituents, such as diamines, cholesterol or other lipophilic groups, or a combination of modifications at these sites. The internucleoside phosphate linkages can include phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate and/or sulfone internucleotide linkages, or 3'-3', 5'-2' or 5'-5' linkages, and combinations of such similar linkages (to produce mixed backbone modified oligonucleotides).

The modifications can be internal (single or repeated) or at the end(s) of the oligonucleotide molecule, and can include additions to the molecule of the internucleoside phosphate linkages, such as cholesteryl, diamine compounds with varying numbers of carbon residues between amino groups and terminal ribose, and deoxyribose and phosphate modifications which cleave or cross-link to the opposite chains or to associated enzymes or other proteins. Electrophilic groups such as ribose-dialdehyde could covalently link with an epsilon amino group of the lysyl-residue of such a protein. A nucleophilic group such as n-ethylmaleimide tethered to an oligomer could covalently attach to the 5' end of an mRNA or to another electrophilic site. The terms "modified oligonucleotides" and "modified polynucleotides" also include oligonucleotides and/or polynucleotides comprising modifications to the sugar moieties (e.g., 2'-substituted or 3'-substituted in the case of 2'-5' linkages). A modified oligonucleotide of the invention (1) does not have the structure of a naturally occurring oligonucleotide and (2) will hybridize preferentially to either RNA or DNA.

The term "oligonucleotide backbone" as used herein refers to the structure of the chemical moiety linking nucleotides in a molecule. Specifically, the term is intended to encompass both the internucleoside phosphate linkage and the ribose group of each monomer. The invention preferably comprises a backbone which is different from a naturally occurring backbone and is further characterized by (1) holding bases in correct sequential order and (2) holding bases a correct distance between each other to allow a natural oligonucleotide to hybridize to it. This may include structures formed from any and all means of chemically linking nucleotides. A modified backbone as used herein includes modifications (relative to natural linkages) to the chemical linkage between nucleotides, as well as other modifications that may be used to enhance stability and affinity, such as modifications to the sugar structure. For example an α-anomer of deoxyribose may be used, where the base is inverted with respect to the natural β-anomer.

The term "end-blocked" as used herein refers to an oligonucleotide with a chemical modification at the molecular level that prevents the degradation of selected nucleotides, e.g., by nuclease action. This chemical modification is positioned such that it protects the integral portion of the modified oligonucleotide, for example the region of the modified oligonucleotide that is targeted for hybridization (i.e., the test sequence of the oligonucleotide). An end block may be a 3' end block or a 5' end block. For example, a 3' end block may be at the 3'-most position of the molecule, or it may be internal to the 3' ends, provided it is 3' of the integral sequences of the modified oligonucleotide.

The term "substantially nuclease resistant" refers to oligonucleotides that are resistant to nuclease degradation as compared to naturally occurring or unmodified oligonucleotides. Modified oligonucleotides of the invention are at least 1.25 times more resistant to nuclease degradation than their unmodified counterpart, more preferably at least 2 times more resistant, even more preferably at least 5 times more resistant, and most preferably at least 10 times more resistant than their unmodified counterpart. Such substantially nuclease resistant oligonucleotides include, but are not limited to, oligonucleotides having one or more backbone modification such as phosphorothioates, methylphosphonates, ethylphosphotriesters, 2'-O-methylphosphorothioates, 2'-O-methyl-p-ethoxy ribonucleotides, 2'-O-alkyls, 2'-O-alkyl-n(O-alkyl), 3'-O-alkyls, 3'-O-alkyl-n(O-alkyl), 3'-O-methyl ribonucleotides, 2'-fluoros, 2'-deoxy-erythropentofuranosyls, 2'-O-methyl ribonucleosides, methyl carbamates, methyl carbonates, inverted bases (e.g., inverted T's), or chimeric versions of these backbones.

The term "substantially acid resistant" as used herein refers to oligonucleotides that are resistant to acid degradation as compared to unmodified oligonucleotides. Typically, the relative acid resistance of an oligonucleotide will be measured by comparing the percent degradation of a resistant oligonucleotide with the percent degradation of its unmodified counterpart (i.e., a corresponding oligonucleotide with "normal" backbone, bases, and phosphodiester linkages). An oligonucleotide that is acid resistant is preferably at least 1.5 times more resistant to acid degradation, at least 2 times more resistant, even more preferably at least 5 times more resistant, and most preferably at least 10 times more resistant than their unmodified counterpart.

The term "alkyl" as used herein refers to a branched or unbranched saturated hyrdrocarbon chain containing 1–6 carbon atoms, such as methyl, ethyl, propyl, tert-butyl, n-hexyl and the like.

The term "array type" refers to the type of gene represented on the array by the associated test modified oligonucleotides, where the type of gene that is represented on the array is dependent on the intended purpose of the array, e.g., to monitor expression of key human genes, to monitor expression of known oncogenes, etc., i.e., the use for which the array is designed. As such, all of the test modified oligonucleotides on a given array correspond to the same type or category or group of genes. Genes are considered to be of the same type if they share some common linking characteristics, such as: species of origin, e.g., human, mouse, rat, etc.; tissue or cell type of origin, e.g., muscle, neural, dermal, organ, etc.; disease state, e.g., cancer; functions, e.g., protein kinases, tumor supressors and the like; participation in the same normal biological process, e.g., apoptosis, signal transduction, cell cycle regulation, proliferation, differentiation etc.; and the like. For example, one array type is a "cancer array" in which each of the "unique" associated test oligonucleotides correspond to a gene associated with a cancer disease state. Likewise, a "human array" may be an array of test oligonucleotides corresponding to unique tightly regulated human genes. Similarly, an "apoptosis array" may be an array type in which the associated test oligonucleotides correspond to unique genes associated with apoptosis.

The terms "associated oligonucleotide," "associated polynucleotide" and "substrate oligonucleotide" and the like refer to the oligonucleotide or polynucleotide composition that makes up each of the samples associated to the array. Thus, the term "associated oligonucleotide" includes oligonucleotide compositions of unique sequences and/or control or calibrating sequences (e.g., oligonucleotides corresponding to housekeeping genes). The modified oligonucleotide and/or polynucleotide compositions are preferably comprised of single stranded nucleic acid, where all of the nucleic acids in a sample composition may be identical to each other. Alternatively, there may be nucleic acids having two or more sequences in each composition, for example two different modified oligonucleotides that are separate but complementary to each other.

The phrases "specific for deoxyribonucleic acid" and "selectively hybridize to DNA" and the like as used interchangeably herein refer to the ability of a modified oligonucleotide to preferentially recognize a deoxyribonucleic acid binding partner. A modified oligonucleotide or polynucleotide that is specific for DNA is twice as likely, more preferably at least 3 times as likely, and even more preferably 10 times as likely to bind to DNA than to RNA.

The phrases "specific for ribonucleic acid" and "selectively hybridize to RNA" and the like as used interchangeably herein refer to the ability of a modified oligonucleotide to preferentially recognize a deoxyribonucleic acid binding partner. A modified oligonucleotide or polynucleotide that is specific for RNA is twice as likely, more preferably at least 3 times as likely, and even more preferably 10 times as likely to bind to RNA than to DNA.

The Invention in General

Arrays having associated modified oligonucleotides and/or polynucleotides with modified backbone structures with the ability to distinguish between RNA and DNA binding partners are provided. For example, modified oligonucleotides having one or more p-ethoxy internucleoside linkage, and preferably at least 25% p-ethoxy internucleoside linkages, more preferably at least 50% p-ethoxy internucleoside linkages, and more preferably at least 75% p-ethoxy internucleoside linkages showed a significant affinity for DNA as compared to RNA. Such an affinity in a modified oligonucleotide composed of 20 monomer units results in at least a 5-fold increase in binding to a DNA molecule as compared to an RNA molecule having an identical sequence.

In another example, modified oligonucleotides having at least one 2'-5' internucleoside linkage, preferably at least 25% 2'-5' internucleoside linkages, more preferably at least 50% 2'-5' internucleoside linkages, and even more preferably 75% 2'-5' internucleoside linkages, showed a significant affinity for RNA as compared to DNA. This is also true for 2'-5' internucleoside linkages combined with a 3'-substitution, e.g., a 3'-O methyl substitution, in the ribose group of at least one monomer. Such an affinity in a modified oligonucleotide composed of 20 monomer units results in at least a 7-fold increase in binding to a DNA molecule as compared to an RNA molecule having an identical sequence.

Modified oligonucleotides and polynucleotides of the invention also may be acid resistant and/or exonuclease resistant to further decrease the sensitivity of the modified oligonucleotide molecule and to allow reusability of the array. In one embodiment, an exonuclease resistant block is added to the 3' or the 5' end of the modified oligonucleotide or polynucleotide depending on the attachment of the nucleic acid to the substrate. The resulting modified oligonucleotides and/or polynucleotides of the invention bind tightly to their RNA or DNA targets in human biological samples containing both exonucleases and endonucleases.

Acid stable associated modified oligonucleotides and/or polynucleotides of the invention are preferably stable when exposed to a pH of 1–2, while their binding partners are not. This allows an array having associated acid stable oligonucleotides and/or polynucleotides to be exposed to a first sample, treated with an acidic solution applied in any of several possible protocols to free the array from the first binding partner, and reused with a second sample. Direct comparison of two different samples of binding partners using a single array has the advantage of limiting potential experimental variation present when comparing multiple arrays. Performing the experiment with the same sample on the same array allows a confirmation of the results obtained in the first instance, thus effectively confirming results without having variation in the array composition.

Similarly, associated end-blocked modified oligonucleotides and/or polynucleotides display a resistance to nucleases, allowing the arrays to be exposed to DNA nucleases to free the array from a sample of binding partners. An array of the invention having nuclease resistant associated modified oligonucleotides can be treated with an appropriate nuclease and reused with a different or the same sample.

The arrays of the present invention encompass associated modified oligonucleotides chemically modified to be acid stable from a pH of 0.01 to 7.0, and more preferably acid stable in a pH of 1.0 to 6.0, allowing such molecules to retain their structural integrity in acidic environments. These modified oligonucleotides, unlike unsubstituted phosphodiester or phosphorothioate DNA or RNA, exhibit significant acid resistance in solutions with pH as low as 0–1 even at 37° C. Acid stability of this first component coupled with the introduction of 3' and/or 5' acid stable, exonuclease resistant ends, confers several unique properties on these modified oligonucleotides.

Typically, the relative nuclease resistance of a oligonucleotide can be measured by comparing the percent digestion of a resistant oligonucleotide with the percent digestion of its unmodified counterpart (i.e., a corresponding oligonucleotide with "normal" backbone, bases, and phosphodiester linkage). Percent degradation may be determined by using analytical HPLC to assess the loss of full length oligonucleotides, or by any other suitable methods (e.g., by visualizing the products on a sequencing gel using staining, autoradiography, fluorescence, etc., or measuring a shift in optical density). Degradation is generally measured as a function of time.

Comparison between unmodified and modified oligonucleotides can be made by ratioing the percentage of intact modified oligonucleotide to the percentage of intact unmodified oligonucleotide. For example, if, after 15 minutes of exposure to a nuclease, 25% (i.e., 75% degraded) of an unmodified oligonucleotide is intact, and 50% (i.e., 50% degraded) of a modified oligonucleotide is intact, the modified oligonucleotide is said to be 2 times (50% divided by 25%) more resistant to nuclease degradation than is the unmodified oligonucleotide. Generally, a substantially nuclease resistant oligonucleotide will be at least about 1.25 times more resistant to nuclease degradation than an unmodified oligonucleotide with a corresponding sequence, typically at least about 1.5 times more resistant, preferably about 1.75 times more resistant, and more preferably at least about 10 times more resistant after 15 minutes of nuclease exposure.

Percent acid degradation may be determined by using analytical HPLC to assess the loss of full length oligonucleotides, or by any other suitable methods (e.g., by visualizing the products on a sequencing gel using staining, autoradiography, fluorescence, etc., or measuring a shift in optical density). Degradation is generally measured as a function of time.

Comparison between unmodified and modified oligonucleotides can be made by ratioing the percentage of intact modified oligonucleotide to the percentage of intact unmodified oligonucleotide. For example, if, after 30 minutes of exposure to a low pH environment, 25% (i.e., 75% degraded) of an unmodified oligonucleotide is intact, and 50% (i.e., 50% degraded) of a modified oligonucleotide is intact, the modified oligonucleotide is said to be 2 times (50% divided by 25%) more resistant to nuclease degradation than is the unmodified oligonucleotide. Generally, substantially "acid resistant" oligonucleotides will be at least about 1.25 times more resistant to acid degradation than an unmodified oligonucleotide with a corresponding sequence, typically at least about 1.5 times more resistant, preferably about 1.75 more resistant, more preferably at least 5 times more resistant and even more preferably at least about 10 times more resistant after 30 minutes of exposure at 37° C. to a pH of about 1.5 to about 4.5.

In a preferred embodiment, the end-blocked oligonucleotides of the compositions and methods of the invention are substantially nuclease resistant, substantially acid resistant, and display a significant affinity for either RNA or DNA. This embodiment includes oligonucleotides with linkages that confer the specificity to a particular nucleic acid (e.g., p-ethoxy linkages and 2'-5' linkages), as well as other internucleoside linkages such as phosphorothioate, p-isopropyl, phosphodiester, phosphotriester, phosphoramidate, propargyl, siloxane, carbonate, carboxymethylester, acetamidate, carbamate, thioether, bridged phosphoramidate, bridged methylene phosphonate, methylphosphonate, phosphorodithioate, bridged phosphorothioate and/or sulfone internucleotide linkages, 3'-3' or 5'-5' or 5'-2' linkages, and combinations of such similar linkages (to produce mixed backbone modified oligonucleotides). The modified oligonucleotides may also optionally have substitutions such as 2'-O-methylphosphodiesters, 2'-O-alkyl, 2'-O-ethyl, 2'-O-propyl, 2'-O-butyl, 2'-O-alkyl-n(O-alkyl), 2'-methoxyethoxy, 2'-fluoro, 2'-deoxy-erythropentofuranosyl, 3'-O-methyl, 2'-O (CH$_2$CH$_2$O)$_x$CH$_3$, provided the substitutions do not impair the ability of the oligonucleotide to distinguish between RNA and DNA.

This embodiment also includes other modifications that render the oligonucleotides and/or polynucleotides substantially resistant to nuclease activity. Methods of rendering an oligonucleotide nuclease resistant include, but are not limited to, covalently modifying the purine or pyrimidine bases that comprise the oligonucleotide. For example, bases may be methylated, hydroxymethylated, or otherwise substituted (e.g., glycosylated) such that the oligonucleotides comprising the modified bases are rendered substantially nuclease resistant.

Arrays composed of the associated oligonucleotides and/or polynucleotides of the current invention are used for diagnostic and/or prognostic purposes. For example, oligonucleotides of the current invention may be used to detect target DNA sequences in a biological sample by contacting an array of the invention a biological sample under conditions that allow for the hybridization of the DNA-specific modified oligonucleotides of the invention to any complementary DNA present in the sample, and detecting such hybridization. This will allow the identification of specific sequences that are associated with a disease state, such as a mutation in a known oncogene or tumor suppressor gene, or a mutation in a locus such as the globin locus.

Alternatively, the arrays of the invention can be used to determine a disease state associated with altered transcription by specifically identifying the presence and relative abundance of a particular RNA transcript in a biological sample. For example, oligonucleotides of the current invention may be used to detect target RNA sequences in a biological sample by contacting an array of the invention a biological sample under conditions that allow for the hybridization of the RNA-specific modified oligonucleotides of the invention to any complementary RNA present in the sample, and detecting such hybridization. This will allow the identification of excessive transcription associated with a disease or a particular prognosis, e.g., the production of HER-2 in breast cancer.

Associated Oligonucleotide and Polynucleotide Compositiionsof the Arrays

Each associated modified oligonucleotide and/or polynucleotide composition of the pattern present on the surface of the substrate is preferably made up of a set of unique modified polymers, and preferably a unique composition. By "unique composition" is meant a collection or population of single stranded modified oligonucleotides capable of participating in a selective hybridization event under appropriate hybridization conditions, where each of the individual modified oligonucleotides may be the same—have the same nucleotide sequence—or different sequences, for example the modified oligonucleotide composition may consist of two different modified oligonucleotides that are complementary to each other (i.e., the two different oligonucleotides are complementary but physically separated so as to be single stranded, i.e., not hybridized to each other). In many embodiments, the modified oligonucleotide compositions will comprise two complementary, single stranded polymers.

In those compositions having unique modified oligonucleotides, the sequence of the modified oligonucleotides are chosen in view of the type and the intended use of the array on which they are present. The unique modified oligonucleotides are preferably chosen so that each distinct unique modified oligonucleotide does not cross-hybridize with any other distinct unique modified oligonucleotide on the array, i.e., it will not cross-hybridize to any other modified oligonucleotide compositions that correspond to a different gene falling within the broad category or type of genes represented on the array under appropriate conditions. As such, the nucleotide sequence of each unique modified oligonucleotide of a composition will have less than 90% homology, usually less than 85% homology, and more usually less than 80% homology with any other different associated modified oligonucleotide composition of the array, where homology is determined by sequence analysis comparison using the FASTA program using default settings. The sequence of unique associated modified oligonucleotides in the compositions are not conserved sequences found in a number of different genes (at least two), where a conserved sequence is defined as a stretch of from about 4 to about 80 nucleotides which have at least about 90% sequence identity, where sequence identity is measured as above. The associated modified oligonucleotide will generally have a length of from about 80 to about 300 bases, usually from 100 to about 200 bases. The length of the nucleic acid can be chosen to best provide binding to the test sequence.

Although in a preferred embodiment the associated modified oligonucleotide composition will not cross-hybridize with any other associated modified oligonucleotides on the array under standard hybridization conditions, associated modified oligonucleotides and hybridization conditions can be altered to allow binding to multiple associated modified oligonucleotide compositions. For example, in determining the relatedness of a sample to oligonucleotides representing different members of a class of proteins, the oligonucleotide sequences may be more similar and/or less stringent hybridization conditions may be used.

Oligonucleotide and Polynucleotide Synthesis

Oligonucleotides can be synthesized on commercially purchased DNA synthesizers from <1 uM to >1 mM scales using standard chemistries and methods that are well known in the art, such as, for example, those disclosed in Stec et al., *J. Am. Chem. Soc.* 106:6077–6089 (1984), Stec et al., *J. Org.*

Chem. 50(20):3908–3913 (1985), Stec et al., *J. Chromatog.* 326:263–280 (1985), LaPlanche et al., *Nuc. Acid. Res.* 14(22):9081–9093 (1986), and Fasman, *Practical Handbook of Biochemistry and Molecular Biology*, 1989, CRC Press, Boca Raton, Fla., herein incorporated by reference.

Oligonucleotides can be deprotected following manufacturer's protocols. Unpurified modified oligonucleotides may be dried down under vacuum or precipitated and then dried. Sodium salts of modified oligonucleotides can be prepared using the commercially available DNA-Mate (Barkosigan Inc.) reagents or conventional techniques such as a commercially available exchange resin, e.g., Dowex, or by addition of sodium salts followed by precipitation, diafiltration, or gel filtration, etc.

Oligonucleotides to be purified can be chromatographed on commercially available reverse phase or ion exchange media, e.g., Waters Protein Pak, Pharmacia's Source Q, etc. Peak fractions can be combined and the samples desalted and concentrated by means of reverse phase chromatography on poly(styrene-divinylbenzene) based columns like Hamilton's PRP, or Polymer Labs PLRP.

Alternatively, ethanol precipitation, diafiltration, or gel filtration may be used followed by lyophilization or solvent evaporation under vacuum in commercially available instrumentation such as Savant's Speed Vac. Optionally, small amounts of the oligonucleotides may be electrophoretically purified using polyacrylamide gels.

Lyophilized or dried-down preparations of modified oligonucleotides can be dissolved in pyrogen-free, sterile, physiological saline (i.e., 0.85% saline), sterile Sigma water, and filtered through a 0.45 micron Gelman filter (or a sterile 0.2 micron pyrogen-free filter). The described oligonucleotides may be partially or fully substituted with any of a broad variety of chemical groups or linkages including those described in Fasman, *Practical Handbook of Biochemistry and Molecular Biology*, 1989, CRC Press, Boca Raton, Fla.

A variety of standard methods can be used to purify the presently described modified oligonucleotides. In brief, the modified oligonucleotides of the present invention can be purified by chromatography on commercially available reverse phase (for example, see the RAININ Instrument Co., Inc. instruction manual for the DYNAMAX®-300A, Pure-DNA reverse-phase columns, 1989, or current updates thereof, herein incorporated by reference) or ion exchange media such as Waters' Protein Pak or Pharmacia's Source Q (see generally, Warren and Vella, 1994, "Analysis and Purification of Synthetic Nucleic Acids by High-Performance Liquid Chromatography", in *Methods in Molecular Biology*, vol. 26; *Protocols for Nucleic Acid Conjugates*, S. Agrawal, Ed., Humana Press, Inc., Totowa, N.J.; Aharon et al., 1993, *J. Chrom.* 698:293–301; and Millipore Technical Bulletin, 1992, *Antisense DNA: Synthesis, Purification, and Analysis*). Peak fractions can be combined and the samples concentrated and desalted via alcohol (ethanol, butanol, isopropanol, and isomers and mixtures thereof, etc.) precipitation, reverse phase chromatography, diafiltration, or gel filtration.

The modified polynucleotides and oligonucleotides that are associated on the array may also be produced used established techniques such as polymerase chain reaction (PCR) and reverse transcription (RT). These methods are similar to those currently known in the art (see e.g., *PCR Strategies*, Michael A. Innis (Editor), et al. (1995) and PCR:*Introduction to Biotechniques Series*, C. R. Newton, A. Graham (1997)), and preferably the enzymes used to produce the polynucleotides or oligonucleotides are optimized for incorporation of modified nucleotide monomers. Methods of identifying which enzymes are best suited for incorporation of nucleotide monomers with specific modifications (e.g., which enzymes will best incorporate 2'-modified dNTPs) are well known in the art, and thus one skilled in the art would be able to identify enzymes for use with the present invention based upon this disclosure. For example, the process directed evolution can be used to unveil mechanisms of both thermal adaptation and incorporation efficiency, and is an effective and efficient approach to identifying optimal enzyme activity. Multiple generations of random mutagenesis, recombination and high throughput can be used to create a polymerase that both incorporates modified nucleotide monomers, e.g.,p-ethoxy substituted dNTPs, and remains thermostable at higher temperatures. See e.g., Zhao H, et al. 12:47–53 (1999).

Other methods of altering catalytic activity include site-directed mutagenesis, codon-level mutagenesis and methods of incorporating deletions or insertions into available enzymes. Genomic sequencing programs may also reveal conserved regions in the enzyme structure and regions of variability between enzymes from closely related species, thus identifying regions of an enzyme that may be altered without affecting the desired activity. It would be well within the skill of one in the art to use such techniques to identify an enzyme with optimal performance for producing the modified polynucleotides and oligonucleotides of the invention.

Techniques for identification of specific enzymes for production of polynucleotides for association on the arrays of the invention are described in Schmidt-Dannert C, et al., *Trends Biotechnol.* 17:135–6 (1999); Moreno-Hagelsieb G, et al., *Biol Res.*29:127–40 (1996); Colacino F, et al., *Biotechnol Genet Eng Rev.* 14:211–77 (1997); Soberon X. *Nat Biotechnol.* 17:539–40 (1999); Arnold F H, et al., *Ann N Y Acad Sci.* 870:400–3 (1999); and Joo H, et al., *Nature* 399:670–3 (1999), each of which are incorporated herein by reference to describe such techniques and enzyme design.

An modified oligonucleotide or polynucleotide is considered pure when it has been isolated so as to be substantially free of, inter alia, incomplete products produced during the synthesis of the desired modified oligonucleotide or polynucleotide. Preferably, a purified modified oligonucleotide or polynucleotide will also be substantially free of contaminants which may hinder or otherwise mask the binding activity of the molecule.

Array Construction

The arrays of the subject invention have a plurality of associated modified modified oligonucleotides and/or polynucleotides stably associated with a surface of a solid support, e.g., covalently attached to the surface with or without a linker molecule. Each associated sample on the array comprises a modified oligonucleotide composition, of known identity, usually of known sequence, as described in greater detail below. Any conceivable substrate may be employed in the invention.

In the arrays of the invention, the modified oligonucleotide compositions are stably associated with the surface of a solid support, where the support may be a flexible or rigid solid support. By "stably associated" is meant that the sample of associated modified oligonucleotides and/or polynucleotides maintain their position relative to the solid support under hybridization and washing conditions. As such, the samples can be non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like. Examples of covalent binding include covalent bonds formed between the oligonucleotides and a functional group present on the surface of the rigid support (e.g., —OH), where the functional group may be naturally occurring or present as a member of an introduced linking group, as described in greater detail below.

As mentioned above, the array is present on either a flexible or rigid substrate. A flexible substrate is capable of being bent, folded or similarly manipulated without breakage. Examples of solid materials which are flexible solid supports with respect to the present invention include membranes, e.g., nylon, flexible plastic films, and the like. By "rigid" is meant that the support is solid and does not readily bend, i.e., the support is not flexible. As such, the rigid substrates of the subject arrays are sufficient to provide physical support and structure to the associated modified oligonucleotides and/or polynucleotides present thereon under the assay conditions in which the array is employed, particularly under high throughput handling conditions. Furthermore, when the rigid supports of the subject invention are bent, they are prone to breakage.

The substrate may be biological, nonbiological, organic, inorganic, or a combination of any of these, existing as particles, strands, precipitates, gels, sheets, tubing, spheres, containers, capillaries, pads, slices, films, plates, slides, etc. The substrate may have any convenient shape, such as a disc, square, sphere, circle, etc.

The substrate is preferably flat but may take on a variety of alternative surface configurations. For example, the substrate may contain raised or depressed regions on which the synthesis takes place. The substrate and its surface preferably form a rigid support on which to carry out the reactions described herein. The substrate and its surface are also chosen to provide appropriate light-absorbing characteristics. For instance, the substrate may be a polymerized Langmuir Blodgett film, functionalized glass, Si, Ge, GaAs, GaP, $SiO_2$, $SIN_4$, modified silicon, or any one of a wide variety of gels or polymers such as (poly) tetrafluoroethylene, (poly)vinylidenedifluoride, polystyrene, polycarbonate, or combinations thereof. Other substrate materials will be readily apparent to those of skill in the art upon review of this disclosure.

In a preferred embodiment the substrate is flat glass or single-crystal silicon with surface relief features of less than 10 angstroms. According to some embodiments, the surface of the substrate is etched using well known techniques to provide for desired surface features. For example, by way of the formation of trenches, v-grooves, mesa structures, or the like, the synthesis regions may be more closely placed within the focus point of impinging light, be provided with reflective "mirror" structures for maximization of light collection from fluorescent sources, etc.

Surfaces on the solid substrate will usually, though not always, be composed of the same material as the substrate. Alternatively, the surface may be composed of any of a wide variety of materials, for example, polymers, plastics, resins, polysaccharides, silica or silica-based materials, carbon, metals, inorganic glasses, membranes, or any of the above-listed substrate materials. In some embodiments the surface may provide for the use of caged binding members which are attached firmly to the surface of the substrate. Preferably, the surface will contain reactive groups, which could be carboxyl, amino, hydroxyl, or the like. Most preferably, the surface will be optically transparent and will have surface Si—OH functionalities, such as are found on silica surfaces.

The surface of the substrate is preferably provided with a layer of linker molecules, although it will be understood that the linker molecules are not required elements of the invention. The linker molecules are preferably of sufficient length to permit modified oligonucleotides and/or polynucleotides of the invention and on a substrate to hybridize to natural nucleic acid molecules and to interact freely with molecules exposed to the substrate. The linker molecules should be 6–50 atoms long to provide sufficient exposure. The linker molecules may also be, for example, aryl acetylene, ethylene glycol oligomers containing 2–10 monomer units, diamines, diacids, amino acids, or combinations thereof. Other linker molecules which can bind to modified oligonucleotides of the invention may be used in light of this disclosure.

The linker molecules can be attached to the substrate via carbon-carbon bonds using, for example, (poly) trifluorochloroethylene surfaces, or preferably, by siloxane bonds (using, for example, glass or silicon oxide surfaces). Siloxane bonds with the surface of the substrate may be formed in one embodiment via reactions of linker molecules bearing trichlorosilyl groups. The linker molecules may optionally be attached in an ordered array, i.e., as parts of the head groups in a polymerized Langmuir Blodgett film. In alternative embodiments, the linker molecules are adsorbed to the surface of the substrate.

In one embodiment of the present invention, the linker molecules and modified nucleotides used herein are provided with a functional group to which is bound a protective group. Preferably, the protective group is on the distal or terminal end of the linker molecule opposite the substrate. The protective group may be either a negative protective group (i.e., the protective group renders the linker molecules less reactive with a monomer upon exposure) or a positive protective group (i.e., the protective group renders the linker molecules more reactive with a monomer upon exposure). In the case of negative protective groups an additional step of reactivation will be required. In some embodiments, this will be done by heating. The protective group on the linker molecules may be selected from a wide variety of positive light-reactive groups preferably including nitro aromatic compounds such as o-nitrobenzyl derivatives or benzylsulfonyl. In a preferred embodiment, 6-nitroveratryloxycarbonyl (NVOC), 2-nitrobenzyloxycarbonyl (NBOC) or α,α-dimethyl-dimethoxybenzyloxycarbonyl (DDZ) is used. Photoremovable protective groups are described in, for example, Patchornik, *J. Am. Chem. Soc.* (1970) 92:6333 and Amit et al., *J. Org. Chem.* (1974) 39:192, both of which are incorporated herein by reference.

The substrate, the region for attachment of an individual oligonucleotide group could be of any size or shape. For example, squares, ellipsoids, rectangles, triangles, circles, or portions thereof, along with irregular geometric shapes, may be utilized. Duplicate synthesis regions may also be applied to a single substrate for purposes of redundancy. The regions on the substrate can have a surface area of between about 1 $cm^2$ and $10^{-10}$ $cm^2$. Preferably, the regions have areas of less than about $10^{-1}$ to $10^{-7}$ $cm^2$, more preferably less than $10^{-3}$ to $10^{-6}$ $cm^2$, and even more preferably less than $10^{-5}$ $cm^2$.

A single substrate supports more than about 10 different modified oligonucleotide and/or polynucleotide compositions and preferably more than about 100 different modified oligonucleotide and/or polynucleotide compositions, although in some embodiments more than about $10^3$, $10^4$, $10^5$, $10^6$, $10^7$, or $10^8$ different compositions are provided on a substrate. Of course, within a region of the substrate in which a modified oligonucleotide or polynucleotide is attached, it is preferred that the modified nucleotides be substantially pure. In preferred embodiments, regions of the substrate contain modified oligonucleotides or polynucleotides which are at least about 50%, preferably 80%, more preferably 90%, and even more preferably, 95% pure. Oligonucleotides or polynucleotides having several sequences can be intentionally provided within a single region so as to provide an initial screening for biological activity, after which materials within regions exhibiting significant binding are further evaluated. In a preferred embodiment, each region will contain a substantially pure modified oligonucleotide or polynucleotide composition having a single sequence.

The substrates of the arrays of the invention comprise at least one surface on which the pattern of associated modified oligonucleotides and/or polynucleotides is present, where the surface may be smooth, substantially planar, or have irregularities, such as depressions or elevations. The surface on which the pattern of associated nucleic acids present may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like.

The amount of modified oligonucleotide or polynucleotide present in each composition will be sufficient to provide for adequate hybridization and detection of nucleic acids during the assay in which the array is employed. Generally, the amount of modified oligonucleotide or polynucleotide in each composition will be at least about 0.1 ng, usually at least about 0.5 ng and more usually at least about 1 ng, where the amount may be as high as 1000 ng or higher, but will usually not exceed about 20 ng and more usually will not exceed about 10 ng. The copy number of each oligonucleotide or polynucleotide in a composition will be sufficient to provide enough hybridization sites to yield a detectable signal, and will generally range from about 0.01 fmol to 50 fmol, usually from about 0.05 fmol to 20 fmol and more usually from about 0.1 fmol to 5 fmol. Where the composition has an overall circular dimension, the diameter of the sample will generally range from about 10 to 5,000 µm, usually from about 20 to 2,000 µm and more usually from about 50 to 1000 µm.

Control composition may be present on the array including compositions comprising oligonucleotides or polynucleotides corresponding to genomic DNA, housekeeping genes, negative and positive control genes, and the like. These latter types of compositions are not "unique" as that term is defined and used herein, i.e., they are "common." In other words, they are calibrating or control genes whose function is not to tell whether a particular "key" gene of interest is expressed, but rather to provide other useful information, such as background or basal level of expression. The percentage of samples which are made of unique oligonucleotides or polynucleotide that correspond to the same type of gene is generally at least about 30%, and usually at least about 60% and more usually at least about 80%. Preferably, the arrays of the present invention will be of a specific type, where representative array types include: human arrays, mouse arrays, cancer arrays, apoptosis arrays, human stress arrays, oncogene and tumor suppressor arrays, cell-cell interaction arrays, cytokine and cytokine receptor arrays, rat arrays, blood arrays, mouse stress arrays, neuroarrays, and the like.

With respect to the modified oligonucleotide and/or polynucleotide compositions that correspond to a particular type or kind of gene, type or kind can refer to a plurality of different characterizing features, where such features include: species specific genes, where specific species of interest include eukaryotic species, such as mice, rats, rabbits, pigs, primates, humans, etc.; function specific genes, where such genes include oncogenes, apoptosis genes, cytokines, receptors, protein kinases, etc.; genes specific for or involved in a particular biological process, such as apoptosis, differentiation, cell cycle regulation, cancer, aging, proliferation, etc.; location specific genes, where locations include organs, such as heart, liver, prostate, lung etc.; tissue, such as nerve, muscle, connective, etc.; cellular, such as axonal, lymphocytic, etc.; or subcellular locations, e.g., nucleus, endoplasmic reticulum, Golgi complex, endosome, lyosome, peroxisome, mitochondria, cytoplasm, cytoskeleton, plasma membrane, extracellular space; specific genes that change expression level over time, e.g., genes that are expressed at different levels during the progression of a disease condition, such as prostate genes which are induced or repressed during the progression of prostate cancer.

In a preferred embodiment, longer oligonucleotides, preferably from 80–300 nt in length, more preferably from 100–200 nt in length, are used on the arrays. These are especially useful in place of cDNAs for determining the presence of mRNA in a sample, as the modified oligonucleotides have the advantage of rapid synthesis and purification and analysis prior to attachments to the substrate surface. In particular, oligonucleotides with 2'-5' linkages or 2'-modified sugar groups show increased binding affinity with RNA, and these oligonucleotides are particularly advantageous in identifying mRNA in a sample exposed to an array.

The length of the modified oligonucleotides allows the compositions to bind with the same affinity as a much longer unmodified nucleic acid, e.g. an unmodified cDNA. In the case where additional complementarity is needed to certain domains or regions found in cDNA, multiple oligonucleotides may be used. Multiple oligonucleotides directed at a particular gene or RNA molecule may be interspersed in a single region, or the different oligonucleotides may each be in a discrete region, e.g. to determine presence or absence of related molecules in a sample.

As mentioned above, the arrays of the present invention typically comprise one or more additional associated oligonucleotide composition which does not correspond to the array type, i.e., the type or kind of gene represented on the array. In other words, the array may comprise one or more compositions that are made of non "unique" oligonucleotides, e.g., oligonucleotides corresponding to commonly expressed genes. For example, compositions comprising oligonucleotides that bind to plasmid and bacteriophage oligonucleotides, oligonucleotides which bind to genes from the same or another species which are not expressed and do not cross-hybridize with the test nucleic acid, and the like, may be present and serve as negative controls. In addition, compositions comprising housekeeping genes and other control genes from the same or another species may be present, e.g., to serve in the normalization of mRNA abundance and standardization of hybridization signal intensity in the sample assayed with the array.

Patents and patent applications describing arrays of oligonucleotides and methods for their fabrication include: U.S. Pat. Nos. 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,895; 5,624,711; 5,639,603; 5,658,734; 5,700,637; 5,744,305; 5,837,832; 5,843,655; 5,861,242; 5,874,974; 5,885,837; WO 93/17126; WO 95/11995; WO 95/35505; EP 742 287; and EP 799 897. Patents and patent applications describing methods of using arrays in various applications include: U.S. Pat. Nos. 5,143,854; 5,288,644; 5,324,633; 5,432,049; 5,470,710; 5,492,806; 5,503,980; 5,510,270; 5,525,464; 5,547,839; 5,580,732; 5,661,028; 5,848,659; 5,874,219; WO 95/21265; WO 96/31622; WO 97/10365; WO 97/27317; EP 373 203; and EP 785 280. References that disclose the synthesis of arrays and reagents for use with arrays include: Matteucci M. D. and Caruthers M. H., *J. Am. Chem. Soc.* (1981) 103:3185–3191; Beaucage S. L. and Caruthers M. H., *Tetrahedron Letters*, (1981) 22(20):1859–1862; Adams S. P. et al., *J. Am. Chem. Soc.* (1983) 105:661–663; Sproat D. S. and Brown D. M., *Nucleic Acids Research*, (1985) 13(8):2979–2987; Crea R. and Horn T., *Nucleic Acids Research*, (1980) 8(10):2331–48; Andrus A. et al., *Tetrahedron Letters*, (1988) 29(8):861–4; Applied Biosystems *User Bulletin*, Issue No. 43, Oct. 1, 1987, "Methyl phosphonamidite reagents and the synthesis and purification of methyl phosphonate analogs of DNA"; Miller P. S. et al., *Nucleic Acids Research*, (1983) 11:6225–6242. Each of these is incorporated herein by reference as exemplary methods of construction and use of arrays of the present invention. The methods of these publications can be readily modified to produce the arrays of the invention with the modified oligonucleotides of the invention on their surface.

In a preferred embodiment, the modified oligonucleotides for use with the present invention are synthesized prior to attachment onto the substrate. This affords the advantages that: (1) oligonucleotides of known composition and sequence can be produced; (2) oligonucleotides can be analyzed and purified prior to attachment, which eliminates "shortmers," i.e., oligonucleotides with insufficient length and/or incorrect sequence; (3) the methods used to produce oligonucleotides are less prone to error than current methods for production of cDNA, e.g. PCR with Taq polymerase, and (4) attachment to the substrate may be monitored or assayed without destroying the array.

Numerous methods can be used for attachment of the oligonucleotides of the invention to the substrate. For example, modified oligonucleotides can be attached using the techniques of, for example U.S. Pat. No. 5,807,522, which is incorporated herein by reference for teaching methods of polymer attachment. Other similar methods may be used, as will be apparent to one skilled in the art upon reading the present technology.

Use of Arrays of the Invention

Oligonucleotide and/or polynucleotide arrays provide a high throughput technique that can assay a large number of polynucleotides in a sample. A variety of different array formats have been developed and are known to those of skill in the art. The arrays of the subject invention find use in a variety of applications, including gene expression analysis, drug screening, mutation analysis and the like.

Arrays can be used, for example, to examine differential expression of genes and can be used to determine gene function. For example, arrays can be used to detect differential expression of a polynucleotide between a test cell and control cell (e.g., cancer cells and normal cells). For example, high expression of a particular message in a cancer cell, which is not observed in a corresponding normal cell, can indicate a cancer specific gene product. Exemplary uses of arrays are further described in, for example, Pappalarado et al., *Sem. Radiation Oncol.* 8:217 (1998), and Ramsay, *Nature Biotechnol.* 16:40 (1998).

In addition the arrays and methods of the present invention can be applied to the identification of infection by and prognosis of a disease caused by any number of microorganisms including bacteria, parasites, and other infectious agents. This may be especially useful in the determination of a particular strain of an infectious organism, e.g., the strain of Human Immunodeficiency Virus (HIV) or bacteria from an infected individual. Determination of the particular infectious microorganism can aid in prognosis of the disease as well as in the treatment of the individual, e.g., a particular strain can determine the aggressiveness of treatment of an infected individual as well as providing a rational basis for the selection of a therapeutic regime. Moreover, the methods of the present invention, by having the ability to distinguish between DNA and RNA in a sample, can be used determine the level of "active" infection, e.g., viral replication. For example, people infected with a virus such as Epstein-Barr may not display any phenotype, as the virus is dormant, yet the viral DNA sequences would be present in the cells of a biological sample. An array with the ability to distinguish between RNA and DNA will allow the identification of viral transcription associated with a disease state, such as mononucleosis, without the background of the viral DNA.

The method of the present invention can also be applied to the analysis of any nucleic acid containing entity, including subcellular organelles such as chloroplasts and mitochondria. Such methods may be useful for determining disorders associated with mitochondrial mutations (e.g., ornithine trans-carbamylase deficiency) or for evolutionary studies involving mutation rates in organelles, such as mapping of mitochondrial DNA.

In a case where the genetic material is available in limited quantity, the arrays having polymers that preferentially bind to a particular nucleic acids can allow the direct detection of a nucleic acid in a cellular extract without a prior amplification step.

Further, the method of the present invention can also be used in screening methods for evaluation of predispositions for disorders and the use and/or efficacy of therapeutic treatments for the treatment or prevention of such disorders, e.g. Alzheimer's disease, Huntington's disease, cancer predispositions such as Li-Fraumeni syndrome, and the like. For example, a specific allele of the apolipoprotein gene, apoE4, is associated with an increased risk for development of Alzheimer's disease (M. Kanai et al., Neurosci Lett. (1999) 267:65–8; Mirra S S. Hum Pathol. (1999) 30:1125–7). The present method provides an efficient and inexpensive method for determining the presence or absence of this allele in an individual, and thus can be predictive of the disease in an individual. Moreover, certain therapeutic agents may be particularly effective for an individual having a particular allele, such as the apoE4 allele, and so identification of the allele also identifies an individual who is a good candidate for treatment with a particular therapy.

Additionally, phylogenetic relationships can be established by the method of the present invention. Phylogenetic analysis can be carried out with almost any selected genomic sequence, such as, glycolytic enzymes (like phosphoglycerate kinase (Vohra, et al.)) or rRNA sequences. Phylogenetic relationships between plants can be established, using, for example, sequences derived from plastid ribosomal RNA operons (Wolfe, et al.).

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test nucleic acids from the remaining data. The resulting data can be displayed as an image with the intensity in each region varying according to the binding affinity between associated oligonucleotides and/or polynucleotides and the test nucleic acids.

Oligonucleotides having a sequence unique to that gene are preferably used in the present invention. Different methods may be employed to choose the specific region of the gene to be targeted. A rational design approach may also be employed to choose the optimal oligonucleotide sequence for the hybridization array. Preferably, the region of the gene that is selected is chosen based on the following criteria. First, the sequence that is chosen should yield an oligonucleotide composition that preferably does not cross-hybridize with any other oligonucleotide composition present on the array. Second, the sequence should be chosen such that the oligonucleotide composition has a low probability of cross-hybridizing with an oligonucleotide having a nucleotide sequence found in any other gene, whether or not the gene is to be represented on the array from the same species of origin, e.g., for a human array, the sequence will not be present in any other human genes. As such, sequences that are avoided include those found in: highly expressed gene products, structural RNAs, repeated sequences found in the sample to be tested with the array and sequences found in vectors. A further consideration is to select oligonucleotides with sequences that provide for minimal or no secondary structure, structure which allows for optimal hybridization but low non-specific binding, equal or similar thermal stabilities, and optimal hybridization characteristics.

The arrays of the present invention can also be used as capture probes in a sandwich assay to selectively identify and immobilize particular DNA or RNA molecules within a sample. The DNA or RNA is preferably labeled with a molecule, such as a fluorophore that aloows detection of the particular molecule. See e.g., Pilevar S et al., *Anal Chem.* 70:2031–7 (1998). The label of the biomolecule may also require a secondary capture species to activate the label and to produce a signal.

Hybridization and Detection

Following preparation of the test nucleic acids from the tissue or cell of interest, the test sample is contacted with the array under hybridization conditions, where such conditions can be adjusted, as desired, to provide for an optimum level of specificity in view of the particular assay being performed. In analyzing the differences in the population of labeled test binding agents generated from two or more physiological sources using the arrays described above, each population of labeled test samples are separately contacted to identical arrays or together to the same array under conditions of hybridization, preferably under stringent hybridization conditions (for example, at 50° C. or higher and 0.1×SSC (15 mM sodium chloride/01.5 mM sodium citrate)), such that test nucleic acids hybridize to complementary oligonucleotides and/or polynucleotides on the substrate surface.

Where all of the test nucleic acids have the same label, different arrays can be employed for each physiological source. Preferably, the same array can be employed sequentially for each physiological source, with test samples removed from the array as described below. Alternatively, where the labels of the test nucleic acids are different and distinguishable for each of the different physiological sources being assayed, the opportunity arises to use the same array at the same time for each of the different test populations. Examples of distinguishable labels are well known in the art and include: two or more different emission wavelength fluorescent dyes, like Cy3 and Cy5, two or more isotopes with different energies of emission, like $^{32}P$ and $^{33}P$, labels which generate signals under different treatment conditions, like temperature, pH, treatment by additional chemical agents, etc., or generate signals at different time points after treatment. Using one or more enzymes for signal generation allows for the use of an even greater variety of distinguishable labels, based on different substrate specificity of enzymes (e.g., alkaline phosphatase/peroxidase).

Following hybridization, non-hybridized labeled nucleic acid is removed from the support surface, conveniently by washing, generating a pattern of hybridized oligonucleotide and/or polynucleotide on the substrate surface. A variety of wash solutions are known to those of skill in the art and may be used. The resultant hybridization patterns of labeled, hybridized oligonucleotides and/or polynucleotides may be visualized or detected in a variety of ways, with the particular manner of detection being chosen based on the particular label of the test nucleic acid, where representative detection means include scintillation counting, autoradiography, fluorescence measurement, calorimetric measurement, light emission measurement and the like.

Following detection or visualization, the hybridization patterns may be compared to identify differences between the patterns. Where arrays in which each of the different oligonucleotides and/or polynucleotides corresponds to a known gene are employed, any discrepancies can be related to a differential expression of a particular gene in the physiological sources being compared.

Clearing of Test Nucleic Acids from Array

Following binding and visualization of a test sample on an array, the array may be treated to remove the bound test nucleic acids. The associated nucleic acid compositions remain intact following treatment, allowing reuse of the treated array. The array of the invention substantially retains its binding capabilities, and any differences in binding ability may be determined using control sequences associated on the array. Preferably, the array of the invention retains at least 75% of its binding capabilities, more preferably the array retains at least 85% of its binding capabilities, and even more preferably the array of the invention retains at least 95% of its binding capabilities.

Arrays with associated modified oligonucleotide and/or polynucleotide compositions can be exposed to a low pH environment, e.g, pH from 0.5–4.5, which results in the degradation of non-modified nucleic acids. Following the treatment, the arrays of the invention are rinsed to remove any unwanted test nucleic acid fragments, residual label and the like, and the arrays are prepared for reuse.

After detection of the test sample is complete, the array may be regenerated by removal and/or degradation of the test sample. For example, a two hour incubation of the sample-bound array in an acid solution at pH 1.5, 39° C., results in complete loss of a full-length unmodified 14-mer oligonucleotide. Under these conditions the bound array oligonucleotides of the invention maintain full length structural integrity. Following the acid incubation, a variety of wash conditions may be used to clear the test sample from the probe array. For example, increased temperature incubation of a low salt wash solution would result in the dissociation of short test fragments from the array. Alternatively, a chemical denaturant (e.g., urea) could be used as a was to remove the test sample. Additional steps, such as an alkaline solution rinse may also be added to the protocol to speed up the cycle time for regeneration.

The above-described washes and rinses can be avoided if the acid incubation is increased resulting in almost complete degradation of the test sample under conditions where the array probe maintains its integrity. Actual incubation times required will vary somewhat from array type to array type, and may be shorter than those given below. As a consequence of the degradation of the test sample the array probe/test sample hybrids become unstable under experimental conditions and may be removed using rinses of the hybridization or stringent wash buffer.

Exemplary clearing conditions for use with the arrays of the invention are:

(1) Incubation of the bound array with pH 1–2 acid solution, 8 hours at 39° C. Follow with three rinses at 39° C. with stringent wash buffer, 0.1×SSC pH 7.0, and two rinses with hybridization buffer, pH approximately 7.0. These two solutions are for removal of degraded sample and the regeneration of the substrate array and hence do not require a low pH. Array may then be reused.

(2) Incubation of the bound array with pH 1–2 acid solution, 4 hours at 39° C. Follow with three 15 minute rinses at 39° C. with 8.0 molar urea. Rinse once with stringent wash buffer, and twice with hybridization buffer. Array can be reused at this point.

(3) Incubation of the bound array with pH 1–2 acid solution, 4 hours at 39° C. Rinse twice at 39° C. with stringent wash buffer. Incubate 20 minutes in 60° C. stringent wash buffer, and rinse twice more with 60° C. stringent wash buffer. Rinse twice with hybridization buffer. Array can be reused at this point.

(4) Incubation of the bound array with pH 1–2 acid solution, 4 hours at 39° C. Rinse twice with stringent wash buffer. Wash twice with 39° C. alkaline solution for 15 minutes followed by two washes with stringent wash buffer. Incubate 20 minutes in 60° C. stringent wash buffer. Rinse twice more with 60° C. stringent wash buffer, and twice with hybridization buffer. Array can be reused at this point.

(5) Incubation of the bound array with nuclease (actual conditions vary with nuclease type) at 37° C. for 1 hour. Wash twice with protein denaturing solution for 20 minutes. Rinse twice with stringent wash buffer. Incubate 20 minutes in 60° C. stringent wash buffer. Rinse twice with 60° C. stringent wash buffer. Rinse twice with hybridization buffer. Array can be reused at this point.

(6) Incubation of the bound array with pH 10–13 base solution (e.g., NaOH) at room temperature for 1–30 minutes followed by additional washes with pH 10–13 base solutions, water, or acidic solution washes followed by a buffer wash.

(7) Incubation of the bound array with a pH 10 base solution (e.g., NaOH) at room 5 temperature, followed by 10 minutes in pH 3 HCl aqueous solution, followed by 4 washes with the pH 10 base solution, then a final wash with hybridization buffer.

Following treatment, the associated modified oligonucleotides of the array remain 1) associated to the substrate surface; 2) structurally intact; and 3) capable of binding with another test binding partner.

In addition, as an alternative way, arrays with associated modified oligonucleotides characterized as nuclease resistant may be treated with a nuclease to remove bound test nucleic acids and label. The nuclease used can be chosen depending on the nature of the binding between the associated modified oligonucleotide and/or polynucleotide and the molecules of the test sample and the attachment of the modified oligonucleotide and/or polynucleotide to the array. For example, if the associated modified oligonucleotides are end-blocked oligonucleotides, and the test sample is comprised of mRNA molecules, then the appropriate nuclease would be one that recognizes RNA-DNA hybrids, e.g., Ribonuclease H. In another example, if the associated modified oligonucleotides are end-blocked oligonucleotides, and the test sample is comprised of cDNA molecules, then the appropriate nuclease would be one that recognizes double stranded DNA complexes, e.g., Deoxyribonuclease I or II, and Exodeoxyribonuclease III or V. In yet another example, if the associated modified oligonucleotides are end-blocked cRNA and the test sample is comprised of mRNA, the appropriate nuclease is one that recognizes RNA-RNA hybrids, such as micrococcal nuclease. Similarly, nucleases that are 5' or 3' specific may be chosen depending on the attachment site of the oligonucleotide and/or polynucleotide to the array. Since the modified oligonucleotides of this embodiment of the invention are nuclease-resistant, the test samples will be specifically targeted and degraded by the nuclease.

Actual choice of regeneration conditions should take into consideration the type of substrate, the type of attachment of probe to substrate, test sample type, and whether there are clearing time constraints. In cases where the substrate is acid sensitive it would be more advantageous to use nuclease digestion to remove the test sample from the array. Such modifications would be well within the skill of one in the art upon reading the present disclosure and description of the subject arrays.

Arrays Stably Associated with Beads

The arrays of the present invention may also be stably associated with beads, and in particular magnetic beads. Such beads can be used as an "array" in a magnetic hybridization assay. In brief, the beads can be produced such that 1) each bead has a multiplicity of oligonucleotides having a single sequence and 2) each bead is specific for a particular nucleic acid, i.e. RNA or DNA. Having the array on beads allows both the detection of specific nucleic acids and the isolation of the same nucleic acids. Optionally, each bead is further recognizable as specific for the particular nucleic acid, i.e. a bead having associated p-ethoxy oligonucleotides is differentially labeled (e.g. by fluorescence) from a bead having associated oligonucleotides having 2'-5' linkages.

The bead array may be composed of a plurality of beads each having a different sequence or, alternatively, each of the beads may have a same sequence. For example, where it is desirable to test for multiple genetic sequences, such as testing for different HLA haplotypes, each bead may have p-ethoxy oligonucleotides with sequences different from any other bead. In another example, where it is desirable to both identify and isolate transcripts from a sample, each bead may have, 2'-5'linked oligonucleotides specific for a different mRNA species. In yet another example, an array may contain beads that each have oligonucleotides with 2'-5' linkages and the same sequence, e.g. to remove a specific mRNA from a sample.

A key element of any magnetic hybridization assay is a system for capturing the magnetic beads. Magnetic beads are, or typically contain, paramagnetic (that is, magnetizable in the presence of an external magnetic field, but nonmagnetic on removal of the field) magnetite ($Fe_3O_4$). Magnetic beads may range in diameter from 50 nm (colloidal "ferrofluids") to several microns. Ferrofluids are so small that they require magnetic fields greater than 4 Tesla per cm to capture them.

A number of different methods can be used to isolate the beads following exposure to the sample. Relatively large field strengths may be generated by a small diameter wire that creates a high field gradient when placed in an external magnetic field. The small diameter wire acts as an antenna to concentrate the magnetic fields near it. A number of existing immunomagnetic separation and detection methods and apparatus rely on this observation. One method has been to place steel wool inside a collecting vessel and then place the vessel inside a strong magnetic field. Another method has been to place paperclip-shaped bent metal pins inside microtiter wells and then move the holder for the microtiter wells-inside a strong magnetic field. In the presence of the enhanced magnetic gradients, magnetic beads can be captured from any fluid samples inside the vessel or microtiter wells onto the steel wool or the bent metal pins. After the magnetic fields are removed, the captured magnetic beads can be removed from the steel wool or bent pins by various techniques. A third method described in the prior art for concentrating magnetic fields is a quadrupole magnetic arrangement which concentrates a magnetic field near the intersection of two north-and two south poles of four bar magnets brought in close proximity. These and other methods, as will be apparent to one skilled in the art, can be used to separate the beads following exposure to a sample. Alternatively non-magnetic beads with density>water, i.e. <1.0 can be used. These can be isolated easily by centrifuging briefly in a benchtop centrifuge. The beads will be pelleted. They can be easily washed and then centrifuged again. This step can be repeated as many times as needed.

Following isolation of the beads, the nucleic acid species that have hybridized to the bead can be isolated and examined for the level of each transcript. For example, the beads can be boiled to remove the bound transcripts from the bead, and the isolated RNA can be examined using techniques such as electrophoresis, asymmetric PCR, mass spectrometry and the like. In another example, the transcripts can be removed from the beads via acid or nuclease treatment and the beads analyzed for the sequence of interest by hybridization of the beads to a rigid arrays having sequences complementary to all of the sequences that were in the original bead array.

EXAMPLES

The present invention and its particular embodiments are illustrated in the following examples. The examples are not intended to limit the scope of this invention but are presented to illustrate and support the claims of this present invention.

Example 1

Synthesis and Purification of Modified Nucleic Acids

Oligonucleotides having 2'-5' linkages and 3'-methoxy substitutions were synthesized using commercial phosphoramidites on commercially purchased DNA synthesizers from <1 uM to >1 mM scales using standard phosphoramidite chemistry and methods that are well known in the art, such as, for example, those disclosed in Stec et al., *J. Am. Chem. Soc.* 106:6077–6089 (1984), Stec et al., *J. Org. Chem.* 50(20):3908–3913 (1985), Stec et al., *J. Chromatog.* 326:263–280 (1985), LaPlanche et al., *Nuc. Acid Res.* 14(22):9081–9093 (1986), and Fasman, *Practical Handbook of Biochemistry and Molecular Biology*, 1989, CRC Press, Boca Raton, Fla., herein incorporated by reference.

Oligonucleotides were deprotected following phosphoramidite manufacturer's protocols. Unpurified oligonucleotides were either dried down under vacuum or precipitated and then dried. Sodium salts of oligonucleotides were prepared using the commercially available DNA-Mate (Barkosigan Inc.) reagents or conventional techniques such as commercially available exchange resin, e.g., Dowex, or by addition of sodium salts followed by precipitation, diafiltration, or gel filtration, etc.

A variety of standard methods were used to purify and produce the presently described oligonucleotides. In brief, oligonucleotides were purified by chromatography on commercially available reverse phase (for example, see the RAININ Instrument Co., Inc. instruction manual for the DYNAMAX®-300A, Pure-DNA reverse-phase columns, 1989, or current updates thereof, herein incorporated by reference) or ion exchange media such as Waters' Protein Pak or Pharmacia's Source Q (see generally Warren and Vella, 1994, "Analysis and Purification of Synthetic Nucleic Acids by High-Performance Liquid Chromatography", in *Methods in Molecular Biology*, vol. 26; *Protocols for Nucleic Acid Conjugates*, S. Agrawal, Ed. Humana Press, Inc., Totowa, N.J.; Aharon et al., 1993, *J. Chrom.* 698:293–301; and Millipore Technical Bulletin, 1992, *Antisense DNA: Synthesis, Purification, and Analysis*). Peak fractions were combined and the samples were concentrated and desalted via alcohol (ethanol, butanol, isopropanol, and isomers and mixtures thereof, etc.) precipitation, reverse phase chromatography, diafiltration, or gel filtration or size-exclusion chromatography.

Lyophilized or dried-down preparations of oligonucleotides were dissolved in pyrogen-free, sterile, physiological saline (i.e., 0.85% saline), sterile Sigma water, and filtered through a 0.45 micron Gelman filter.

The p-ethoxy oligonucleotides were synthesized in a small scale prep (1.5 $\mu$M) using standard chemistry. The p-ethoxy oligonucleotides were deprotected with $NH_4OH$ by treatment with 28% $NH_4OH$ at room temperature for 1 hour with occasional swirling. The $NH_4OH$ is removed, and the process repeated twice with fresh $NH_4OH$. Following the last treatment, the p-ethoxy oligonucleotides were filtered through a 0.45 micron filter and refrigerated.

Approximately 1 ml of 1 M NaCl, pH 10 was added per 0.4 ml of $NH_4OH$ deprotected oligonucleotide. The sample was loaded onto a PRP-1 column, washed with water until the conductivity is below 25 $\mu$S/cm, and then eluted with an ethanol gradient 0–70% ethanol in 14 minutes. The ethanol was removed by dessication of the sample in a speed vac without heat. Following dessication a solution of 1:1 ratio EDA:ethanol was added to the oligonucleotide, and the resuspended oligonucleotide was incubated for 6 hours at room temperature. Following incubation, the sample was refrigerated until use.

EDA:ethanol removal was accomplished by a further dilution of the oligonucleotide in two volumes of pH 10 1 M NaCl and then loading the sample onto a PRP-1 column. The column is again washed and eluted as described above, and the elute evaporated without heat in a speed vac. The oligonucleotide may then be precipitated with salt and ethanol or chromatographed. If the oligonucleotide is chromatographed over a SAX column, the phases used were 0.03 M NaCl, pH 10 and 2.0 M NaCl, pH 10. The eluted sample is then desalted over another PRP-1 column as described.

Example 2

Specificity of Different Modified Oligonucleotides

The binding specificity of 20-mer modified oligonucleotides (5'-ggt ggt tcc tcc tca gtc gg-3'; SEQ ID NO:1) to its RNA or DNA complement (5'-ccg act gag aag gaa cca cc-3'; SEQ ID NO:2) were tested in a solution having 10 mM $NaPO_4$ with three different NaCl concentrations: no salt, 100 mM NaCl, and 1 M NaCl. The RNA or DNA test molecules were labeled with a fluorescent label, Oregon Green 488, to allow detection of these molecules upon hybridization to the test sequences. Following hybridization, the level of binding of each of these molecules was determined by the level of Oregon Green 488 that was detectable on the controlled pore glass (CPG) beads having the specific modified oligonucleotides.

Results were as follows:

TABLE 1

Binding of Polymers Having Different Backbones with RNA and DNA
Sample numbers are shown in parenthesis.

| Binding Partners | | No salt | 100 mM NaCl | 1000 mM NaCl |
| --- | --- | --- | --- | --- |
| 2'-O-Me | DNA | (1) 133207 | (2) 86762 | (3) 82122 |
| 2'-O-Me | RNA | (4) 54299 | (5) 96307 | (6) 91018 |
| 2'-5' linkage, 3'-O-Me | DNA | (7) 480 | (8) 916 | (9) 1278 |
| 2'-5' linkage, 3'-O-Me | RNA | (10) 7487 | (11) 92603 | (12) 90092 |
| 2'-O-Me 2-amino Adenosine | DNA | (13) 9106 | (14) 84645 | (15) 85377 |
| 2'-O-Me 2-amino Adenosine | RNA | (16) 44508 | (17) 96492 | (18) 91949 |
| p-ethoxy | DNA | (19) 47988 | (20) 90058 | (21) 82827 |
| p-ethoxy | RNA | (22) 1137 | (23) 14273 | (24) 10838 |
| 2'-O-Me p-ethoxy | DNA | (25) 33876 | (26) 93641 | (27) 88624 |
| DNA | DNA | (28) 15478 | (29) 87692 | (30) 83432 |
| DNA | RNA | (31) 12435 | (32) 77390 | (33) 80184 |
| 2'-O-Me p-ethoxy | RNA | (34) 79967 | (35) 102109 | (36) 95661 |

The data is also shown in graphical format in FIG. 1.

As can be seen from the above data, p-ethoxy internucleoside linkages confer upon modified oligonucleotides the ability to selectively hybridize to DNA, whereas 2'-5' internucleoside linkages confer upon modified oligonucleotides the ability to selectively hybridize to RNA.

Example 3

Isoation and Detection Using a Bead Array

Magnetic beads are coated with 2'-5'linked 3'-methoxy substituted oligonucleotides having sequences complementary to transcripts of genes known to be involved in breast cancer, such as HER-2, p53, ras and the like. Each bead is coated with multiple copies of an oligonucleotide having the same gene-specific sequence. Approximately 100 ng of each oligonucleotide are added to 1 µg of coated magnetic beads and incubated for 10 minutes. Magnetic beads were collected using a cobalt magnet and washed in PBS, followed by resuspension in 1 ml PBS, and the beads combined for the creation of the bead array. All incubations are performed with gentle agitation or vortex mixing at room temperature.

Cells taken from a breast tumor are assayed by exposing 1 ml samples of homogenized tumor tissue and 1 ml of homogenized normal breast tissue, diluted 1:10 in PBS, with 1 to 2 µg of the bead array for 1 hour at room temperature and washed three times in PBS prior to processing. The beads are then separated from the sample using an apparatus such as that described in U.S. Pat. No. 5,972,721. Typical runs consist of a 2 minute magnetic collection cycle, a 1 minute rinse cycle, and a 4 minute expulsion of captured materials by vibration of the flow cell. The fluid flow rate is maintained at approximately 2 ml per minute. The transcript-oligonucleotide-magnetic bead complexes are efficiently captured by a high magnetic field gradient.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. An array comprising a plurality of modified oligonucleotide compositions stably associated with the surface of a support, wherein each oligonucleotide composition is characterized by:
   an oligonucleotide backbone structure modified from that of a naturally occurring nucleotide polymer, comprising at least one p-ethoxy internucleoside linkage, wherein the oligonucleotides of the composition are characterized by a binding affinity greater than that of a corresponding, non-modified oligonucleotide, wherein the oligonucleotides are further characterized by a pH stability of at least one hour at 37° C. at a pH range of about 0.5 to about 6.0; and
   wherein the oligonucleotides of the composition selectively hybridize to DNA.

2. An array comprising a plurality of modified oligonucleotide compositions stably associated with the surface of a support, wherein each oligonucleotide composition is characterized by:
   an oligonucleotide backbone structure modified from that of a naturally occurring nucleotide polymer, comprising at least one 2'-5'-internucleoside linkage and one 3'-O-methyl substituent,
   wherein the oligonucleotides of the composition are characterized by a binding affinity greater than that of a corresponding, non-modified oligonucleotide, wherein the oligonucleotides are further characterized by a pH stability of at least one hour at 37° C. at a pH range of about 0.5 to about 6.0; and
   wherein the oligonucleotides of the composition selectively hybridize to RNA.

3. The array of claim 1 or 2, wherein the oligonucleotides are comprised of a modification at a 2' site of the sugar group of at least one nucleotide.

4. The array of claim 1 or 2, wherein the oligonucleotides further comprise a blocking chemical modification at or near at least one end of said oligonucleotides, and wherein the oligonucleotides are further characterized by a nuclease resistance of at least twice that of a naturally occurring oligonucleotide having the same sequence and number of bases.

5. The array of claim 1 or 2, wherein said modified oligonucleotides have an average length of from about 80 to about 300 nucleotides.

6. The array of claim 1 or 2, wherein said modified oligonucleotides have an average length of from about 100 to about 200 nucleotides.

7. The array of claim 1 or 2, wherein oligonucleotides of each of said oligonucleotide compositions have a different sequence from oligonucleotides of any other oligonucleotide composition on the array.

8. The array of claim 1 or 2, wherein each oligonucleotide composition comprises a population of identical oligonucleotides.

9. The array of claim 1 or 2, wherein each oligonucleotide composition comprises a plurality of oligonucleotides that bind to a particular nucleic acid.

10. The array of claim 1 or 2, wherein the number of oligonucleotide compositions on said array ranges from about 10 to about $10^8$.

11. The array of claim 1 wherein each modified oligonucleotide comprises at least 25% p-ethoxy internucleoside linkages.

12. The array of claim 1 wherein each modified oligonucleotide comprises at least 50% p-ethoxy internucleoside linkages.

13. The array of claim 1 or 2 wherein the modified oligonucleotides are modified at each monomer unit.

14. The array of claim 2, wherein each modified oligonucleotide comprises at least 25% 2'-5' internucleoside linkages.

15. The array of claim 2, wherein each modified oligonucleotide comprises at least 50% 2'-5' internucleoside linkages.

16. A method for selectively identifying DNA in a biological sample which contains DNA, comprising:
   a) contacting said sample with the array of claim 1;
   b) allowing the DNA in the biological sample to hybridize to a modified sequence of the array; and
   c) analyzing the results of the hybridizing.

17. A method for selectively identifying RNA in a biological sample which contains RNA, comprising:
   a) contacting said sample with the array of claim 2;
   b) allowing the DNA in the biological sample to hybridize to a modified sequence of the array; and
   c) analyzing the results of the hybridizing.

18. The method of claim 16 or 17 further comprising:
   d) removing sequences hybridized to sequences of the array using a removing agent selected from the group consisting of a solution having a pH of less than 6.0 and a nuclease which enzymatically destroys natural nucleic acid sequences; and
   e) repeating (a), (b), (c) and (d) with a second biological sample.

* * * * *